(12) United States Patent
Yamamoto et al.

(10) Patent No.: US 10,150,966 B2
(45) Date of Patent: Dec. 11, 2018

(54) RNA SEQUENCE HAVING ANTI-TUMOUR ACTIVITY

(71) Applicants: Hirofumi Yamamoto, Suita-shi, Osaka (JP); Masaki Mori, Suita-shi, Osaka (JP)

(72) Inventors: Hirofumi Yamamoto, Suita (JP); Masaki Mori, Suita (JP); Yuichiro Doki, Suita (JP)

(73) Assignees: Hirofumi Yamamoto, Suita-shi, Osaka (JP); Masaki Mori, Suita-shi, Osaka (JP)

( * ) Notice: Subject to any disclaimer, the term of this patent is extended or adjusted under 35 U.S.C. 154(b) by 0 days.

(21) Appl. No.: 15/123,623

(22) PCT Filed: Mar. 4, 2015

(86) PCT No.: PCT/JP2015/056352
§ 371 (c)(1),
(2) Date: Sep. 2, 2016

(87) PCT Pub. No.: WO2015/133521
PCT Pub. Date: Sep. 11, 2015

(65) Prior Publication Data
US 2017/0073675 A1    Mar. 16, 2017

(30) Foreign Application Priority Data
Mar. 4, 2014 (JP) ................................. 2014-041769

(51) Int. Cl.
| A61K 48/00 | (2006.01) |
| C07H 21/02 | (2006.01) |
| C07H 21/04 | (2006.01) |
| C12N 15/113 | (2010.01) |
| A61K 47/02 | (2006.01) |
| A61K 9/00 | (2006.01) |
| A61K 9/51 | (2006.01) |

(52) U.S. Cl.
CPC .......... *C12N 15/113* (2013.01); *A61K 9/0019* (2013.01); *A61K 9/5115* (2013.01); *A61K 47/02* (2013.01); *C12N 2310/141* (2013.01); *C12N 2310/351* (2013.01)

(58) Field of Classification Search
CPC .... A61K 48/00; A61K 31/713; C12N 15/113; C12N 2310/11
See application file for complete search history.

(56) References Cited

U.S. PATENT DOCUMENTS

| 8,586,726 B2* | 11/2013 | Califano | C12N 15/113 536/23.1 |
| 2012/0251619 A1 | 10/2012 | Gunaratne | |
| 2014/0363469 A1 | 12/2014 | Meyers et al. | |

FOREIGN PATENT DOCUMENTS

| JP | 2006-509838 | 3/2006 |
| WO | WO 2004/043495 A1 | 5/2004 |
| WO | WO 2011/130464 A1 | 10/2011 |
| WO | WO 2013-109604 | 7/2013 |

OTHER PUBLICATIONS

Sun et al., Cell Physiol Biochem, 2015, 37, 707-718.*
Fang, et al. 2011 "MicroRNA-29b suppresses tumor angiogenesis, invasion, and metastasis by regulating matrix metalloproteinase 2 expression" *Hepatology* 54(5): 1729-1740.
Poudyal, et al. 2013 "A key role of microRNA-29b for the suppression of colon cancer cell migration" *PLOS ONE* 8(10): 1-9.
Huang, X. et al. 2013 "Targeted Delivery of microRNA-29b by Transferrin-Conjugated Anionic Lipopolyplex Nanoparticles: A Novel Therapeutic Strategy in Acute Myeloid Leukemia" *Clin Cancer Res* 19(9): 2355-67.
International Search Report in Application No. PCT/JP2015/056352, dated Jun. 2, 2015.
Mott, J.L. et al. 2007 "mir-29 regulates Mcl-1 protein expression and apoptosis" *Oncogene* 26: 6133-6140.
Rothschild, S.I. et al. 2012 "MicroRNA-29b is involved in the Src-ID1 signaling pathway and is dysregulated in human lung adenocarcinoma" *Oncogene* 31: 4221-4232.
Wang, Y. et al. 2013 "The role of miRNA-29 family in cancer" *European Journal of Cell Biology* 92: 123-128.
Hossain et al. 2010 "Carbonate apatite-facilitated intracellularly delivered siRNA for efficient knockdown of functional genes" *Journal of Controlled Release* 147: 101-108.
Tavernier et al. 2011 "mRNA as gene therapeutic: How to control protein expression" *Journal of Controlled Release* 150: 238-247.
Written Opinion in corresponding European Application 15757718.0, dated Oct. 4, 2017.

* cited by examiner

*Primary Examiner* — Amy H Bowman
(74) *Attorney, Agent, or Firm* — Knobbe, Martens, Olson & Bear, LLP (57) ABSTRACT

Provided is a novel useful microRNA having improved anti-tumor activity, obtained by introducing a variation in a microRNA which is present in-vivo and which exhibits an anti-tumor effect. This microRNA containing a base sequence (SEQ ID NO: 1) obtained by varying a predetermined region of the base sequence of miR-29b is able to exhibit a particularly outstanding anti-tumor effect.

6 Claims, 10 Drawing Sheets

Specification includes a Sequence Listing.

| | (Day 18) | | | |
|---|---|---|---|---|
| | Cont | sCA-miRcont | sCA-MIRTX | P |
| TP (g/dl) | 5.23±0.45 | 5.25±0.06 | 5.43±0.09 | NS |
| Alb (u/dl) | 3.23±0.33 | 3.18±0.29 | 3.33±0.09 | NS |
| ALP (u/l) | 47.3±4.57 | 40.0±9.56 | 52.5±11.1 | NS |
| ALT (u/l) | 56.0±6.16 | 91.5±74.4 | 48.0±13.9 | NS |
| AMY (u/l) | 924±93.7 | 889±115 | 910±62.5 | NS |
| T-Bil (mg/dl) | 0.30±0.00 | 0.25±0.06 | 0.28±0.05 | NS |
| BUN (mg/dl) | 32.3±4.99 | 26.3±1.26 | 22.5±2.52 | NS |
| Cre (mg/dl) | 0.20±0.00 | 0.20±0.00 | 0.25±0.10 | NS |
| Na (mmol/l) | 148±2.99 | 144±2.87 | 145±3.56 | NS |
| K (mmol/l) | 4.15±0.61 | 4.30±0.55 | 4.10±0.16 | NS |
| Ca (mg/dl) | 9.68±0.41 | 9.93±0.29 | 10.3±0.13 | NS |
| P (mg/dl) | 4.40±0.18 | 4.43±0.29 | 5.70±0.85 | 0.028 |
| Glu (mg/dl) | 213±37.6 | 244±33.5 | 220±42.9 | NS |

FIG. 20

RNA SEQUENCE HAVING ANTI-TUMOUR ACTIVITY

TECHNICAL FIELD

The present invention relates to a novel microRNA having antitumor activity.

A Sequence Listing submitted as an ASCII text file via EFS-Web is hereby incorporated by reference in accordance with 35 U.S.C. § 1.52(e). The name of the ASCII text file for the Sequence Listing is 24146746_1.TXT, the date of creation of the ASCII text file is Sep. 2, 2016, and the size of the ASCII text file is 1.47 KB.

BACKGROUND ART

A microRNA is a small RNA molecule of 18 to 24 nucleotides and is found in a wide range of eukaryotes. About 1,000 human miRNAs have been identified. The miRNA is a short, single-stranded, endogenously-expressed RNA molecule first reported in 1993. From DNA, an RNA molecule having a loop structure is transcribed, which is called pri-miRNA. The loop is cleaved by an enzyme to yield a pre-miRNA. The pre-miRNA is exported from the nucleus. Then, from the pre-miRNA, a miRNA sequence of about 20 to 25 bases is cut out by Dicer. The miRNA sequence is taken in by an RNA-induced silencing complex (RISC), which is a complex of ribonucleic acid and protein Argonaute. As a result, a miRNA-RISC complex is formed, which binds to the 3'UTR of mRNA and suppresses gene expression. The pairing between a miRNA molecule and a mRNA molecule is not perfect, and therefore a single miRNA molecule can have more than one target gene. This means that a single miRNA molecule can be regulated by targeting a plurality of genes, which is an important feature of miRNA.

It is clearly understood that the microRNA plays important roles in regulation of gene expression in a living organism and that aberration in the microRNA-operated regulation system is related to causes and progressions of many diseases. In particular, microRNAs involved in development and progression of cancer have been investigated in their various aspects, and have received much attention as a promising nucleic acid drug for cancer treatment.

Among the microRNAs involved in development and progression of cancer, the miR-29 family is conventionally known to have an excellent antitumor effect, and have received attention as a candidate molecule for clinical application in microRNA replacement therapy against cancer. For example, Non-Patent Document 1 reports that members of the miR-29 family have functions of regulating tumorigenesis and cancer progression. Non-Patent Document 2 reports that administration of miR-29, the sequence of which is complementary to the sequence of the anti-apoptotic gene Mcl-1, successfully suppressed Mcl-1 expression in a cholangiocarcinoma cell and successfully induced apoptosis of the cholangiocarcinoma cell. Non-Patent Document 3 reports that c-Src and ID1, which are signals related to invasion and growth of cancer, are highly expressed in patients with lung cancer and that miR-29b successfully suppresses invasion and growth of cancer in patients with lung cancer by binding to the 3'-UTR region of ID1 and suppressing the c-Src-ID1 signal. Non-Patent Document 4 reports that administration of miR-29b to acute leukemia patients by using transferrin-binding nanoparticles successfully suppressed expressions of oncogenes such as DNMT1, DNMT3A, DNMT3B, SP1, CDK6, FLT3, and KIT in leukemia cells, indicating an antitumor effect.

Cancer is serious and life-threatening disease, therefore nucleic acid drugs for cancer treatment are demanded for further enhancement of their antitumor effect. Conventionally, microRNAs in living organisms have been studied for their practical use as nucleic acid drugs for cancer treatment. However, no sufficient research has been performed to enhance the antitumor effect of microRNAs in living organisms by mutagenesis of the microRNAs.

PRIOR ART DOCUMENTS

Non-Patent Documents

Non-Patent Document 1: Y. Wang et European Journal of Cell Biology, 92 (2013), 123-128
Non-Patent Document 2: Mott et al., Oncogene, 26 (2007), 6133-6140
Non-Patent Document 3: SI Rothschild et al., Oncogene, 31 (2012), 4221-4232
Non-Patent Document 4: Huang X, et al., Clinical Cancer Research, 19 (2013), 2355-2367

SUMMARY OF THE INVENTION

Problems to be Solved by the Invention

An object of the present invention is to provide a novel useful microRNA that possesses an enhanced anti-tumor activity by mutagenesis of microRNA that occurs in a living organism and has an antitumor effect.

Means for Solving the Problem

The inventor of the present invention has conducted intensive research to achieve the object and, as a result, has found that mutagenesis of a certain site in the base sequence of miR-29b yields a novel microRNA having a remarkably enhanced antitumor effect. He has further studied based on this finding and finally has completed the present invention.

The present invention provides an invention having the following embodiments.

Item 1. A microRNA, including a polynucleotide (i) or (ii):
(i) a polynucleotide having a base sequence represented by SEQ ID NO: 1; or
(ii) a polynucleotide having a base sequence having a sequence identity of 70% or higher with the base sequence represented by SEQ ID NO: 1, and the polynucleotide having a comparable level of antitumor effect to the antitumor effect of the polynucleotide consisting of the base sequence represented by SEQ ID NO: 1.

Item 2. The microRNA according to Item 1, wherein
the base sequence of the polynucleotide (ii) is the same as the base sequence represented by SEQ ID NO: 1 but includes substitution or deletion of at least one of 1st, 14th, 20th, and 24th bases from the 5' end of the base sequence represented by SEQ NO: 1, the substitution being substitution by another base(s), the polynucleotide (ii) having a comparable level of antitumor effect to the antitumor effect of the polynucleotide consisting of the base sequence represented by SEQ ID NO: 1.

Item 3. The microRNA according to Item 1, including the polynucleotide having the base sequence represented by SEQ ID NO: 1.

Item 4. The microRNA according to any one of Items 1 to 3, wherein the microRNA is a mature miRNA, a pri-miRNA, or a pre-miRNA.

Item 5. A therapeutic agent for cancer, including the microRNA as claimed in any one of Items 1 to 4 as an active ingredient.

Item 6. The therapeutic agent for cancer according to Item 5, wherein the cancer is solid tumor.

Item 7. The therapeutic agent for cancer according to claim 5 or 6, wherein the microRNA as described in any one of Items 1 to 4 is in the form of complex with carbonate apatite particles.

Item 8. A method of treating cancer, including:
a step of administering an effective amount of a microRNA to a patient with cancer, the microRNA including a polynucleotide (i) or (ii):
(i) a polynucleotide having a base sequence represented by SEQ ID NO: 1; or
(ii) a polynucleotide having a base sequence having a sequence identity of 70% or higher with the base sequence represented by SEQ ID NO: 1, and the polynucleotide having a comparable level of antitumor effect to the antitumor effect of the polynucleotide consisting of the base sequence represented by SEQ ID NO: 1.

Item 9. Use of a microRNA for producing a therapeutic agent for cancer, the microRNA including a polynucleotide (i) or (ii):
(i) a polynucleotide having a base sequence represented by SEQ ID NO: 1; or
(ii) a polynucleotide having a base sequence having a sequence identity of 70% or higher with the base sequence represented by SEQ ID NO: 1, and the polynucleotide having a comparable level of antitumor effect to the antitumor effect of the polynucleotide consisting of the base sequence represented by SEQ ID NO: 1.

Item 10. A microRNA for use in treating cancer, including a polynucleotide (i) or (ii):
(i) a polynucleotide having a base sequence represented by SEQ ID NO: 1; or
(ii) a polynucleotide having a base sequence having a sequence identity of 70% or higher with the base sequence represented by SEQ ID NO: 1, the polynucleotide having a comparable level of antitumor effect to the antitumor effect of the polynucleotide consisting of the base sequence represented by SEQ ID NO: 1.

Advantages of the Invention

The microRNA of the present invention can effectively inhibit proliferation of cancer cells and has excellent antitumor effects. Therefore, the microRNA of the present invention is useful as a nucleic acid drug for cancer treatment. Furthermore, the microRNA of the present invention is highly safe, and therefore has immense clinical benefit.

EMBODIMENTS OF THE INVENTION 1. microRNA

The microRNA of the present invention includes a polynucleotide (i) or (ii):
(i) a polynucleotide having a base sequence represented by SEQ ID NO: 1; or
(ii) a polynucleotide having a base sequence having a sequence identity of 70% or higher with the base sequence represented by SEQ ID NO: 1, and the polynucleotide having a comparable level of antitumor effect to the antitumor effect of the polynucleotide consisting of the base sequence represented by SEQ ID NO: 1.

The base sequence represented by SEQ ID NO: 1 in the polynucleotide (i) is 5'-UCUAAACCACCAUAUGAAAC-CAGC-3', which has a sequence identity of 62.5% with the base sequence of human mature miR-29b-3p.

The polynucleotide (ii) is simply required to have a comparable level of antitumor effect to the polynucleotide consisting of the base sequence represented by SEQ ID NO: 1 and to have a sequence identity of 70% or higher with the base sequence represented by SEQ ID NO: 1. The sequence identity with the base sequence represented by SEQ ID NO: 1 is preferably 80% or higher, more preferably 85% or higher, further preferably 90% or higher, and particularly preferably 95% or higher, for example.

The "identity" between base sequences in the present specification concerns an optimum alignment between 2 nucleotide sequences aligned with the use of a mathematical algorithm known in the technical field, and refers to the proportion identical nucleotide residues in the total nucleotide residues aligned with each other. Specifically speaking, the "identity" between 2 base sequences can be calculated by aligning them with the use of a homology-computation algorithm, NCBI BLAST-2 (National Center for Biotechnology Information Basic Local Alignment Search Tool), with the default search parameter.

Another embodiment of the polynucleotide (ii) is, for example, a polynucleotide having a base sequence that is the same as the base sequence represented by SEQ ID NO: 1 but includes substitution, deletion, insertion, or addition of 1 or several nucleotides, the polynucleotide having a comparable level of antitumor effect to the antitumor effect of the polynucleotide consisting of the base sequence represented by SEQ ID NO: 1. The number of nucleotides subjected to substitution, deletion, insertion, or addition is from 1 to 6, for example, preferably from 1 to 5, more preferably from 1 to 4, further preferably from 1 to 3, and particularly preferably 1 or 2.

In SEQ ID NO: 1, none of the 1st base U, the 14th base A, the 20th base C, and the 24th base C from the 5' end thereof are considered to greatly affect gene interference action. Therefore, examples of another embodiment of the polynucleotide (ii) include polynucleotides in which at least one of 1st, 14th, 20th, and 24th bases from the 5' end of SEQ ID NO: 1 is substituted by another base or deleted and then none of the other bases is substituted or deleted. In other words, examples of another embodiment of the polynucleotide (ii) include polynucleotides having a base sequence 5'-$N_1$CUAAACCACCAU$N_2$UGAAA$N_3$CAG$N_4$-3' (SEQ ID NO: 5), where each of $N_1$, $N_2$, $N_3$ and $N_4$ is any base.

Determination of whether the polynucleotide has "a comparable level of antitumor effect to the antitumor effect of the polynucleotide consisting of the base sequence represented by SEQ ID NO: 1" can be performed by a cell proliferation assay with the use of colorectal cancer cells (the strain DLD-1, the strain SW480, the strain HCT116, the strain HT29, or the strain MIAPaCa-2).

The microRNA of the present invention may be a mature miRNA (mature-miRNA), or may be a hairpin-type miRNA precursor (pri-miRNA) or a pre-miRNA that is a partial pri-miRNA cleaved from the pri-miRNA. The pri-miRNA or the pre-miRNA is processed within a cell to become a mature miRNA. Alternatively, the microRNA of the present invention, together with an RNA molecule having a complementary base sequence, may form a double-stranded precursor. The double strand of the double-stranded precursor breaks within a cancer cell and releases a mature miRNA. The polynucleotide, which the microRNA of the present invention includes, having the base sequence represented by SEQ ID NO: 1 or a mutated base sequence thereof can be used as a mature miRNA. The base sequences of the hairpin-type miRNA precursor and the pre-miRNA are simply required to be designed so that a polynucleotide having the base sequence represented by SEQ ID NO: 1 or a mutated (by substitution, deletion, insertion, or addition of one or several bases) base sequence thereof can be produced as a mature miRNA. Such base sequences can be appropriately designed by those skilled in the art.

Alternatively, the microRNA of the present invention may have various ordinary nucleic-acid modifications, as needed, for properties such as resistance to enzymatic degradation. Examples of the modifications include modification in a sugar chain part, such as 2'-O methylation; modification in a base part; and modification in a phosphoric acid part, such as amination, lower alkyl amination, and acetylation.

2. Therapeutic Agent for Cancer

The microRNA has an excellent antitumor effect and therefore is used as an active ingredient of a therapeutic agent for cancer. In other words, the microRNA can be used as a nucleic acid drug for cancer treatment.

The type of cancer that is treated with the therapeutic agent for cancer of the present invention is not particularly limited as long as the cancer can be targeted by chemotherapy. Specific examples thereof include solid tumors such as colorectal cancer, colon cancer, gastric cancer, rectal cancer, hepatoma, pancreatic cancer, lung cancer, breast cancer, bladder cancer, prostate cancer, cervical cancer, head and neck cancer, cholangiocarcinoma, gallbladder cancer, and oral cancer, and cancers related to blood, such as leukemia and malignant lymphoma. Among these, solid tumors, especially colorectal cancer, are suitably treated with the therapeutic agent for cancer of the present invention.

The method of administering the therapeutic agent for cancer of the present invention is not particularly limited as long as the therapeutic agent for cancer of the present invention can be delivered to cancer tissue or a cancer cell in a living organism. Examples of the method include intravascular (intra-arterial or intravenous) injection, continuous infusion, subcutaneous administration, topical administration, intramuscular administration, and intraperitoneal administration. Among these, intra-arterial or intravenous administration is preferable.

The dose of the therapeutic agent for cancer of the present invention is appropriately determined depending on the type of the cancer, the sex, the age, and the symptom of the patient, and the like, and therefore cannot be determined based on general criteria. Examples of the dose include about mg/m$^2$ to about 100 mg/m$^2$ (surface area of the body) per day in terms of the dose of the microRNA.

The microRNA that is contained in the therapeutic agent for cancer of the present invention is transferred into a cancer cell, where the microRNA expresses its functions and exhibits its antitumor effect. For easy transfer of the microRNA into a cancer cell, the therapeutic agent for cancer of the present invention is desirably a preparation containing a microRNA-introducing agent. The microRNA-introducing agent is not particularly limited and may be any one of carbonate apatite particles, Lipofectamine, Oligofectamine, RNAiFect, and the like. Among these microRNA-introducing agents, carbonate apatite particles can be made accumulated on cancer cells within a living organism and efficiently transferred into the cancer cell. Therefore, a preferable embodiment of the therapeutic agent for cancer of the present invention is one in which the microRNA is mixed with carbonate apatite particles or is present in the form of complex particles of the microRNA and carbonate apatite particles.

Next, the carbonate apatite particles used as the microRNA-introducing agent in the therapeutic agent for cancer of the present invention are described.

(Carbonate Apatite Particles)

Carbonate apatite is a compound of formula $Ca_{10-m}X_m(PO_4)_6(CO_3)_{1-n}Y_n$ that has a structure in which the hydroxyl group of hydroxy apatite $(Ca_{10}(PO_4)_6(OH)_2)$ is partially replaced by $CO_3$. In the formula, X is an element capable of partially replacing Ca in the carbonate apatite, examples of which include Sr, Mn, and rare-earth elements. In the formula, m is generally a positive number of 0 to 1, preferably 0 to 0.1, more preferably 0 to 0.01, even more preferably 0 to 0.001. Y is a group or an element capable of partially replacing $CO_3$ in the carbonate apatite, examples of which include OH, F, and Cl. In the formula, n is generally a positive number of 0 to 0.1, preferably 0 to 0.01, more preferably 0 to 0.001, even more preferably 0 to 0.0001.

The average particle size of the carbonate apatite particles used in the present invention is not particularly limited as long as the carbonate apatite particles can be administered into a living organism and transferred into a colorectal cancer cell. From the viewpoint of accumulation on a colorectal cancer cell within a living organism and efficient transfer into the colorectal cancer cell, the average particle size of the carbonate apatite particles used in the present invention is generally 50 nm or less, preferably from 1 nm to 40 nm, further preferably from 1 nm to 20 nm and more preferably from 5 nm to 10 nm.

The average particle size of the carbonate apatite is the value measured by observation using a scanning probe microscope. Before the measurement of the particle size with the scanning probe microscope the site to be measured should be observed with a CCD camera. As a result, when large particles clearly unsuitable for measurement with a scanning probe microscope are observed (for example, particles with diameters of 5 μm or more), such large particles will be removed from the measurement. As used in the present specification, the term "particle size" means the size of independent particles that can be individually identified when measured with a scanning probe microscope. Therefore, when a plurality of particles form an aggregate, such an aggregate should be counted as a single particle.

The carbonate apatite particles can be obtained by a known method. For example, the carbonate apatite particles can be prepared by making calcium ions, phosphate ions, and hydrogencarbonate ions coexist in an aqueous solution. The concentrations of each type of the ions in the aqueous solution are not particularly limited as long as the carbonate apatite particles can be formed, and may be appropriately set taking into account the followings.

The concentration of calcium ions in the aqueous solution is generally from 0.1 mM to 1000 mM, preferably from 0.5 mM to 100 mM, and further preferably from 1 mM to 10 mM.

The concentration of phosphate ions in the aqueous solution is generally from 0.1 mM to 1000 mM, preferably from 0.5 mM to 100 mM, and further preferably from 1 mM to 10 mM.

The concentration of hydrogencarbonate ions in the aqueous solution is generally from 1.0 mM to 10000 mM, preferably from 5 mM to 1000 mM, and further preferably from 10 mM to 100 mM.

Sources of calcium ions, phosphate ions, and hydrogencarbonate ions are not particularly limited as long as they can supply the ions to the aqueous solution, and examples thereof include water-soluble salts of these ions. More specifically, $CaCl_2$ may be used as a calcium ion source. $NaH_2PO_4 \cdot 2H_2O$ may be used as a phosphate ion source, and $NaHCO_3$ may be used as a carbonate ion source.

The aqueous solution for preparation of the carbonate apatite particles may contain other components than the respective ion sources and an additional substance, as long as the carbonate apatite particles can be formed. For example, fluoride ions, chloride ions, Sr, Mn, or other species may be added to the aqueous solution so that in the composition, such a species can partially replace Ca or $CO_3$ in carbonate apatite. The added amount of fluoride ions, chloride ions, Sr, or Mn is preferably in a range where there is no significant effect on the pH-solubility of the formed complex particles or the particle size range of the formed complex particles. The base material used in the aqueous solution for preparation of the carbonate apatite particles may be water, or may be various cell culture media or buffers, for example.

In preparation of the carbonate apatite particles used in the present invention, the order in which the respective ion sources and the additional substance are mixed into the aqueous solution is not particularly limited, and the aqueous solution may be prepared in any mixing order as long as desired carbonate apatite particles can be obtained. For example, the aqueous solution can be prepared by a process including preparing a first solution containing calcium ions and the additional substance, separately preparing a second solution containing phosphate ions and hydrogencarbonate ions, and mixing the first and second solutions.

The carbonate apatite particles can be obtained by leaving to itself (incubating), for a certain period of time, the aqueous solution containing each type of the ions with the pH of the aqueous solution adjusted to the range of 6.0 to 9.0. In the process of forming the carbonate apatite particles, the pH of the aqueous solution is from 7.0 to 8.5, for example, preferably from 7.1 to 8.5, further preferably from 7.2 to 8.5, furthermore preferably from 7.3 to 8.5, particularly preferably from 7.4 to 8.5, and most preferably from 7.5 to 8.0.

In the process of forming the carbonate apatite particles, the temperature condition of the aqueous solution is not particularly limited as long as the carbonate apatite particles can be formed, and is generally 10° C. or more, preferably from 25° C. to 80° C. and further preferably from 37° C. to 70° C. or higher.

In the process of forming the carbonate apatite particles, the time to incubate the aqueous solution is not particularly limited as long as the carbonate apatite particles can be formed, and is generally from 1 minute to 24 hours and preferably from 10 minutes to 1 hour. Formation of such particles can be checked by observation with a microscope, for example.

The method for regulating the carbonate apatite particles to an average particle size of 50 nm or less is not particularly limited. Examples of the method include a method of ultrasonic vibration treatment of the carbonate apatite particles formed in the aqueous solution. As used herein, the term "ultrasonic vibration treatment" does not refer to a treatment in which ultrasonic waves are applied to a specimen by bringing the specimen into direct contact with an ultrasonic vibrator of an ultrasonic crusher, a homogenizer, or other means for use in what is called cell-disruption or other procedures, but refers to a treatment using an ultrasonic cleaner having an ultrasonic vibrator and a cleaning tank integrated together generally for use in cleaning precision instruments, test tubes, or other objects. The ultrasonic vibration treatment means a process including placing a liquid (such as water) in the cleaning tank (water tank) of an ultrasonic cleaner, allowing a vessel (such as a plastic tube) to float in the liquid, wherein the vessel contains the carbonate apatite particles, and applying ultrasonic waves to an aqueous solution containing the carbonate apatite particles through the liquid in a similar manner to cleaning precision instruments. This process makes it possible to conveniently and efficiently reduce the size of the carbonate apatite particles to 50 nm or less.

The device that can be used in the ultrasonic vibration treatment is not particularly limited as long as it can apply ultrasonic vibration indirectly to a vessel containing the carbonate apatite particles through a solvent such as water, like the ultrasonic cleaner does. In view of versatility and good handle ability, an ultrasonic cleaner having an ultrasonic vibrator and a thermostatic tank is preferably used.

The conditions under which the ultrasonic vibration treatment is performed are not particularly limited as long as the particle size can be regulated to the predetermined range. For example, the temperature of the water tank may be appropriately selected from temperatures ranging from 5° C. to 45° C., preferably from 10° C. to 35° C., and further preferably from 20° C. to 30° C. The high-frequency power in the ultrasonic vibration treatment may be appropriately set in the range from 10 W to 500 W, for example, preferably from 20 W to 400 W, further preferably from 30 W to 300 W, and more preferably from 40 W to 100 W. The oscillating frequency is generally from 10 Hz to 60 Hz, preferably from 20 Hz to 50 Hz, and further preferably from 30 Hz to 40 Hz. The time period of the ultrasonic vibration treatment is within the range from 30 seconds to 30 minutes, for example, preferably within the range from 1 minute to 20 minutes, and further preferably within the range from 3 minutes to 10 minutes.

In the process of performing the ultrasonic vibration treatment, the type of vessel to contain the carbonate apatite particles is not limited as long as the size of the particles can be reduced to the predetermined range of particle size. Such a vessel may be appropriately selected depending on the volume of the aqueous solution or the intended use of the aqueous solution. For example, a plastic tube with a capacity of 1 to 1000 ml may be used.

The ultrasonic vibration treatment is preferably performed in the presence of albumin (in other words, after albumin is added to the aqueous solution containing the carbonate apatite particles). This is because when the ultrasonic vibration treatment is performed in an environment where the carbonate apatite particles coexist with albumin, carbonate apatite nanoparticles with smaller sizes can be obtained, and reaggregation of the particles can also be suppressed. The concentration of albumin in the aqueous solution containing the carbonate apatite particles is not particularly limited as long as the effects of particle size reduction and/or of reaggregation suppression can be obtained. Albumin can be added in an amount from about 0.1 mg/ml to about 500 mg/ml, for example, preferably from about 1 mg/ml to about 100 mg/ml, and further preferably from about 1 mg/ml to about 10 mg/ml.

(Complex Particles of the microRNA and Carbonate Apatite Particles)

In a preferable embodiment of the therapeutic agent for cancer of the present invention, the complex particles of the microRNA and the carbonate apatite particles are used. This form of the microRNA as the complex with the carbonate apatite particles enables the microRNA to be efficiently accumulated on a cancer cell within a living organism by the action of carbonate apatite and be introduced into the cancer cell. In addition, after introduction into the cell, the microRNA can be released from the carbonate apatite particles within the cell, and, as a result, an antitumor effect of the microRNA can be efficiently exhibited.

In the present invention, the complex particles of the microRNA and the carbonate apatite particles refer to the state in which the microRNA is adsorbed and supported on the carbonate apatite particles via an ionic bond, a hydrogen bond, and the like. The method of forming the complex particles of the microRNA and the carbonate apatite particles is not particularly limited. Examples of the method include a method of making the microRNA and the carbonate apatite particles coexist in an aqueous solution; and a method of, in an aqueous solution that is used for preparation of the carbonate apatite particles, making the microRNA coexist with calcium ions, phosphate ions, and hydrogencarbonate ions, so as to simultaneously perform formation of the carbonate apatite particles and formation of the complex of the microRNA and the carbonate apatite particles.

Regarding formation of the complex particles of the microRNA and the carbonate apatite particles, when formation of the carbonate apatite particles and formation of the complex of the microRNA and the carbonate apatite particles are simultaneously performed, the microRNA may be added to the aqueous solution that is used for preparation of carbonate apatite, in an amount from 0.1 nM to 1000 nM, for example, preferably from 0.5 nM to 500 nM, and further preferably from 1 nM to 200 nM.

In the complex particles of the microRNA and the carbonate apatite particles, the ratio of the microRNA to the carbonate apatite particles is not particularly limited, and may be appropriately determined, for example, depending on the dose of the microRNA. In the case of forming a complex that includes the microRNA in an amount of 2 mg and the carbonate apatite particles, for example, 5 mg of the microRNA may be added to 2.5 L of the aqueous solution that is used for preparation of the carbonate apatite particles as described above, so as to simultaneously perform formation of the carbonate apatite particles and formation of the complex of the microRNA and the carbonate apatite particles.

When the microRNA used as the therapeutic agent for colorectal cancer of the present invention is in the form of complex with the carbonate apatite particles, the microRNA is in the state of dispersion in a solvent suitable for administration to a living organism. As described above, the carbonate apatite particles are obtained by dissolving various substances, which are to serve as ion sources, in a solvent such as water, a medium, or a buffer. The resulting solution in which the carbonate apatite particles are thus dispersed is not necessarily suitable for administration to a living organism (intravascular administration) from the viewpoints of osmotic pressure, buffering capacity, sterility, and the like. Therefore, the solvent in which the carbonate apatite particles are dispersed is replaced by a solvent suitable for administration to a living organism (such as physiological saline). For this replacement, a process of separating and recovering the carbonate apatite particles from the solvent by centrifugation and replacing the solvent is generally required. By this process, however, the carbonate apatite particles become aggregated to each other to form large particles, which are, again, not suitable for administration to a living organism. To solve this problem, the aggregated carbonate apatite particles are added to a solvent suitable for administration to a living organism, and then the ultrasonic vibration treatment described above is performed. As a result, the particle size of the complex particles of the microRNA and the carbonate apatite particles dispersed in the solvent suitable for administration to a living organism becomes an appropriate particle size (preferably, an average particle size of 50 nm or less).

When the microRNA used as the therapeutic agent for cancer of the present invention is in the form of complex with the carbonate apatite particles, it is desirable that administration of the therapeutic agent for colorectal cancer of the present invention is performed immediately after the complex particles of the microRNA and the carbonate apatite particles are dispersed by the ultrasonic vibration treatment and before the resulting microparticles become reaggregate. For example, administration is preferably performed within 1 minute, preferably 30 seconds, after the ultrasonic vibration treatment. Alternatively, when albumin is added as described above for suppressing aggregation of the carbonate apatite particles, administration can be performed several minutes to several dozen minutes after the ultrasonic vibration treatment.

EXAMPLES

Next, the present invention will be described based on examples. The scope of the present invention, however, is not limited to the following examples.

Example 1: Evaluation of Antitumor Effect on Human Colorectal Cancer Cell (Strain DLD-1)

In a D-MEM medium (containing FBS in an amount of 10% by volume) within a 24-well plate, human colorectal cancer cells (the strain DLD-1) were inoculated at $5 \times 10^4$ cells/ml, followed by overnight culture at 37° C. Subsequently, MIRTX-Star (a microRNA represented by SEQ ID NO: 1, produced by a known method for polynucleotide synthesis as added to achieve a concentration of 50 nM, followed by culturing with 1.0 μl/well of Lipofectamine RNAIMAX for 24 hours at 37° C. for transfection. Then, the medium was exchanged to a D-MEM medium (containing FBS in an amount of 10% by volume), followed by culturing. The numbers of cells were counted at 24, 48, and 72 hours after transfection. In addition, 48 hours after transfection, the colorectal cancer cells were subjected to DAPI staining and Ki-67 immunostaining. As controls in this test,
a case in which no microRNA was introduced (Parent) and cases in which one of a control microRNA (SEQ ID NO: 2) (NC, negative control), miR-34a (PC, positive control; SEQ ID NO: 3), and miR-29b-3p (SEQ ID NO: 4) was used instead of MIRTX-Star were also tested under the same conditions.

Figure 1:
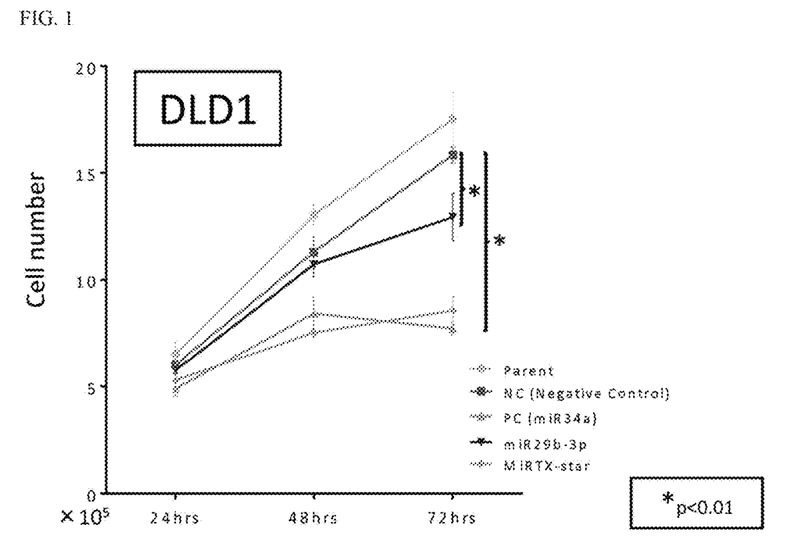
FIG. 1 shows results of Example 1, demonstrating an inhibitory effect of the microRNA of the present invention on proliferation of human colorectal cancer cells (the strain DLD-1).
Figure 2:
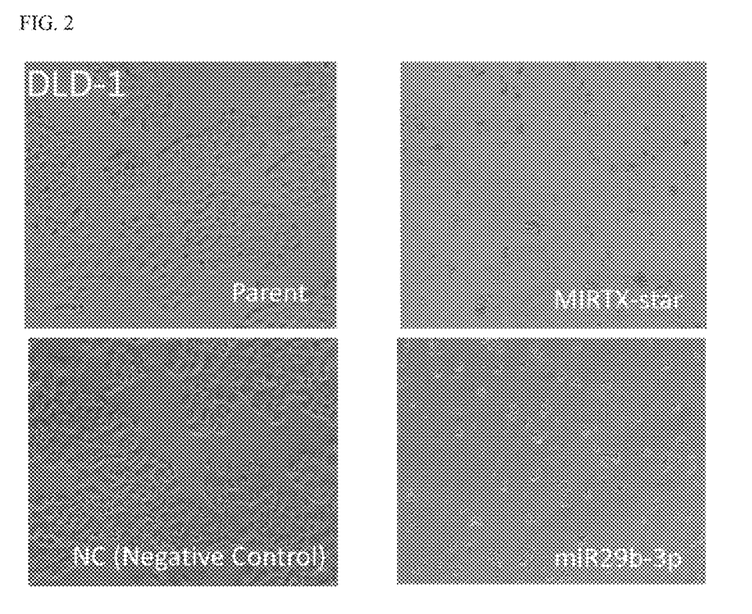
FIG. 2 shows results of Example 1, observing the phenotype of human colorectal cancer cells (the strain DLD-1) in the presence of the microRNA of the present invention.
Figure 3:
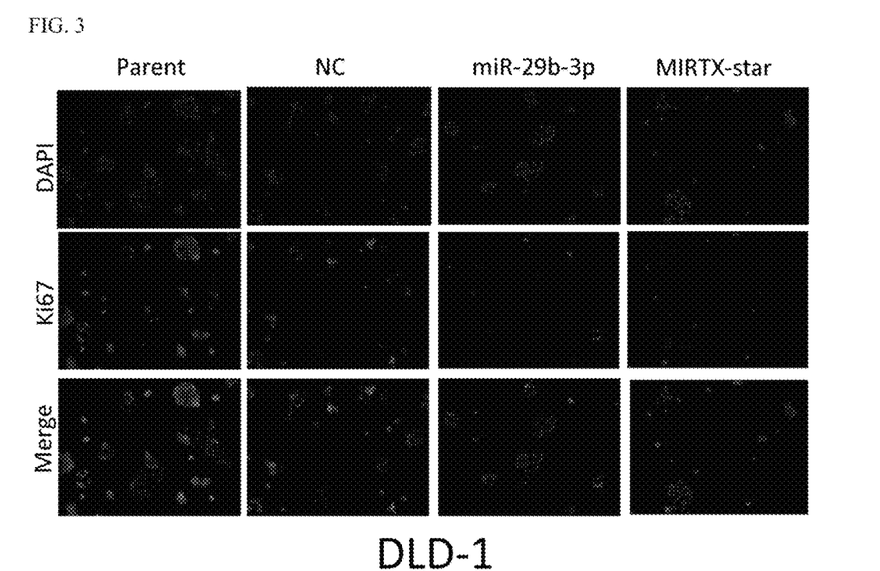
FIG. 3 shows results of Example 1, namely, the results of DAPI staining and Ki-67 immunostaining of human colorectal cancer cells (the strain DLD-1) in the presence of the microRNA of the present invention.

FIG. 1 shows the results of cell numbers. FIG. 2 shows the results of microscopic observation of the phenotype of the cells 72 hours after transfection. 3 shows the results of DAPI staining and Ki-67 immunostaining performed 48 hours after transfection.

These results showed that MIRTX-Star had an inhibitory effect in proliferation of the colorectal cancer cells (the strain DLD-1), and also showed that the inhibitory effect was much greater than that of miR-29b-3p and was comparable to that of miR-34a, miR-34a is known to have an excellent antitumor effect. The results of DAPI staining and Ki-67 immunostaining also showed a remarkable decrease in Ki-67 expression, which is a cell proliferation marker, in the colorectal cancer cells (the strain DLD-1) when transfection with MIRTX-Star was performed.

Example 2: Evaluation of Antitumor Effect on Human Colorectal Cancer Cells (Strain SW480)

An experiment was performed under the same conditions as in Example 1 except that the strain SW480 was used as human colorectal cancer cells.

Figure 4:
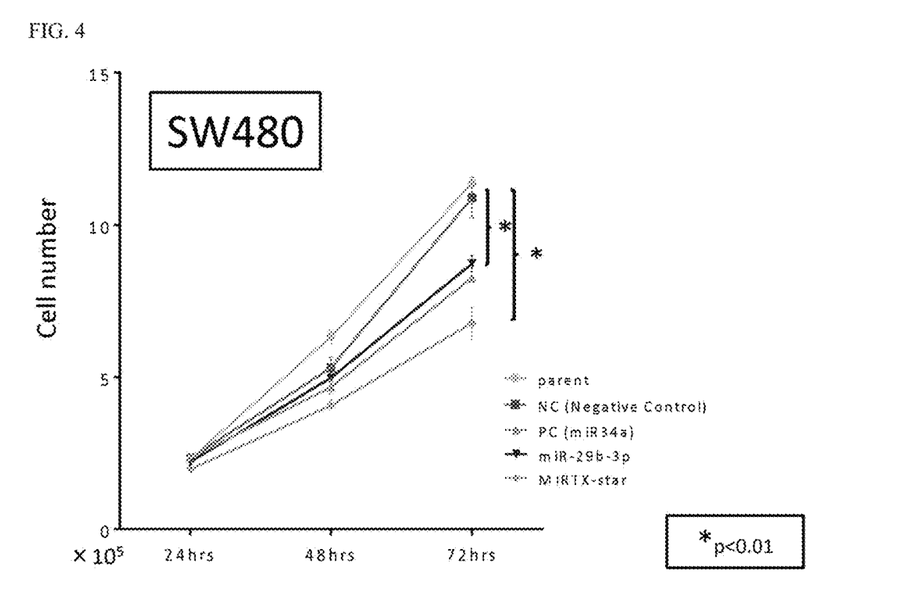
FIG. 4 shows results of Example 2, evaluating an inhibitory effect of the microRNA of the present invention on proliferation of human colorectal cancer cells (the strain SW480).
Figure 5:
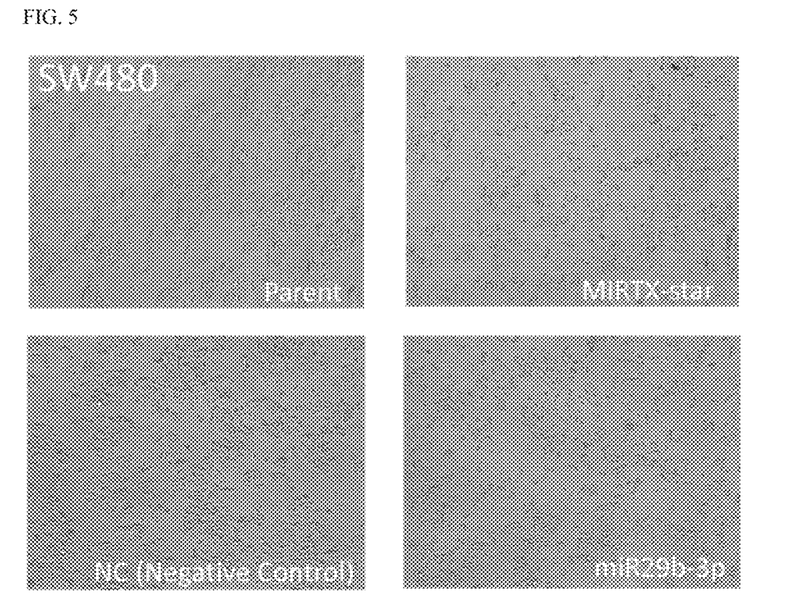
FIG. 5 shows results of Example 2, observing the phenotype of human colorectal cancer cells (the strain SW480) in the presence of the microRNA of the present invention.
Figure 6:
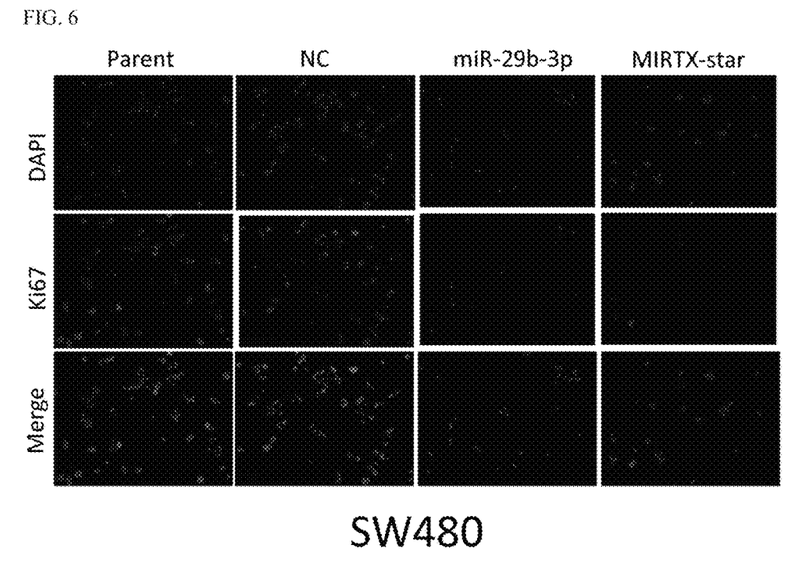
FIG. 6 shows results of Example 2, the results of DAPI staining and Ki-67 immunostaining of human colorectal cancer cells (the strain SW480) cultured in the presence of the microRNA of the present invention.

FIG. 4 shows the results of cell numbers. FIG. 5 shows the results of microscopic observation of the phenotype of the cells 72 hours after transfection. FIG. 6 shows the results of DAPI staining and Ki-67 immunostaining performed 48 hours after transfection. As shown in FIGS. 4 to 6, MIRTX-Star had an effect in inhibiting proliferation of the colorectal cancer cells (the strain SW480) and the effect was much greater than that of miR-34a.

Example 3: Evaluation of Antitumor Effect on Human Colorectal Cancer Cells (Strain HCT116)

An experiment was performed under the same conditions as in Example 1 except that the strain HCT116 was used as human colorectal cancer cells.

Figure 7:
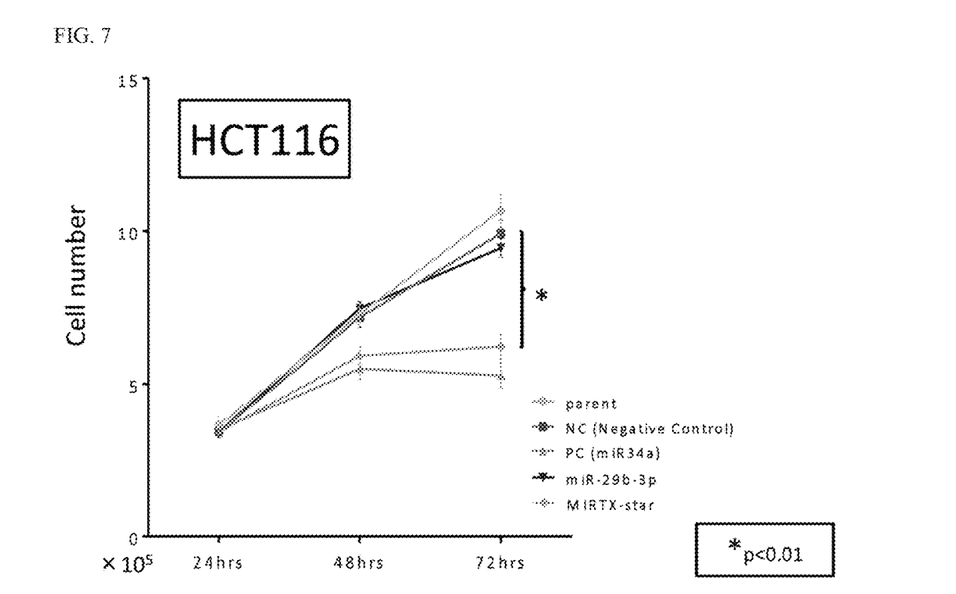
FIG. 7 shows results of Example 3, evaluating an inhibitory effect of the microRNA of the present invention on proliferation of human colorectal cancer cells (the strain HCT116).
Figure 8:
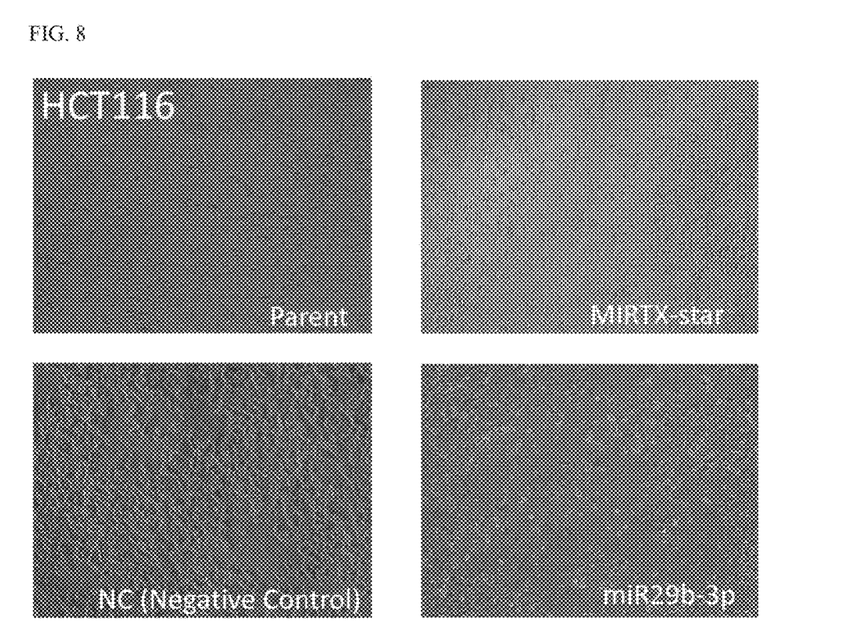
FIG. 8 shows results of Example 3, observing the state of human colorectal cancer cells (the strain HCT116) after culturing the cells in the presence of the microRNA of the present invention.

FIG. 7 shows the results of cell numbers. FIG. 8 shows the results of microscopic observation of the phenotype of the cells 72 hours after transfection. As shown in FIGS. 7 and 8, miR-29b-3p hardly inhibited proliferation of the colorectal cancer cells (the strain HCT116), while MIRTX-Star effectively inhibited proliferation of the colorectal cancer cells (the strain HCT116).

Example 4: Evaluation of Antitumor Effect on Human Colorectal Cancer Cells (Strain HT29)

An experiment was performed under the same conditions as in Example 1 except that the strain HT29 was used as human colorectal cancer cells.

Figure 9:
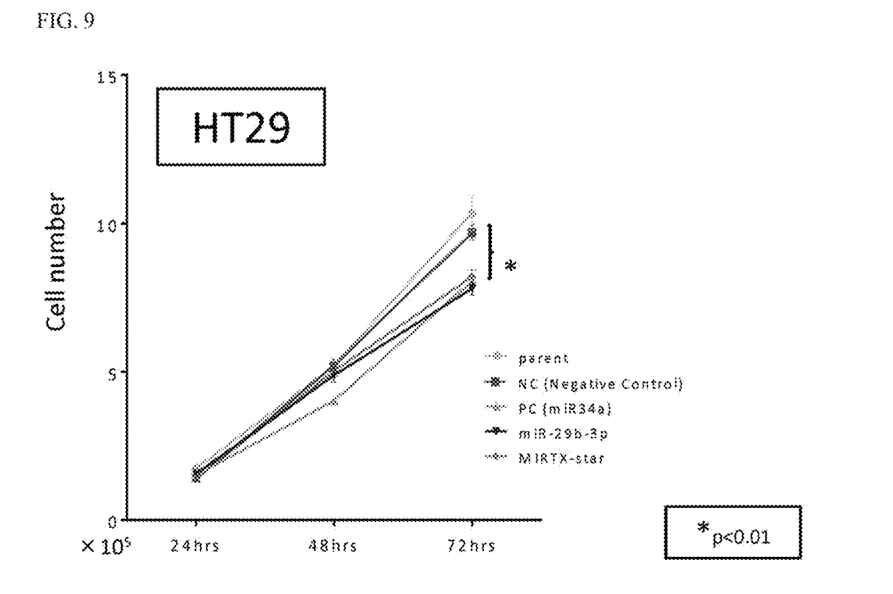
FIG. 9 shows results of Example 4, evaluating an inhibitory effect of the microRNA of the present invention on proliferation of human colorectal cancer cells (the strain HT29).
Figure 10:
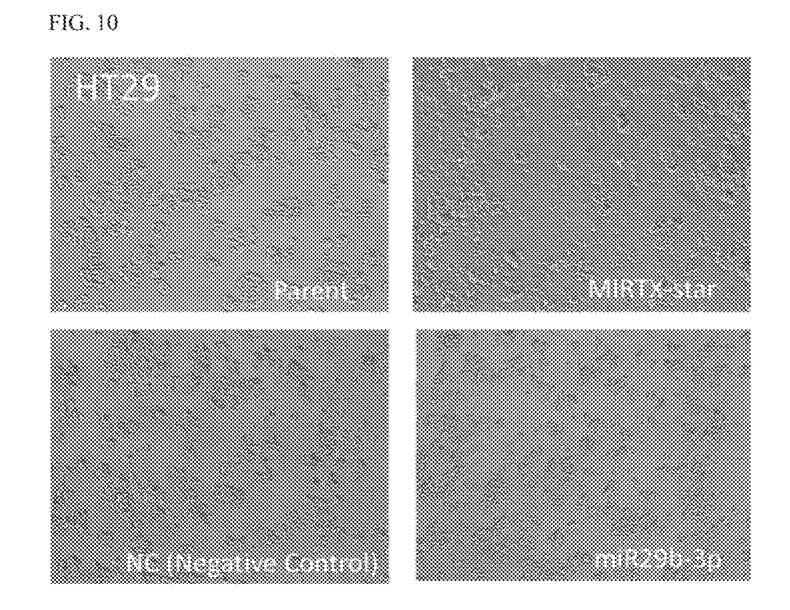
FIG. 10 shows results of Example 4, observing the phenotype of human colorectal cancer cells (the strain HT29) in the presence of the microRNA of the present invention.
Figure 11:
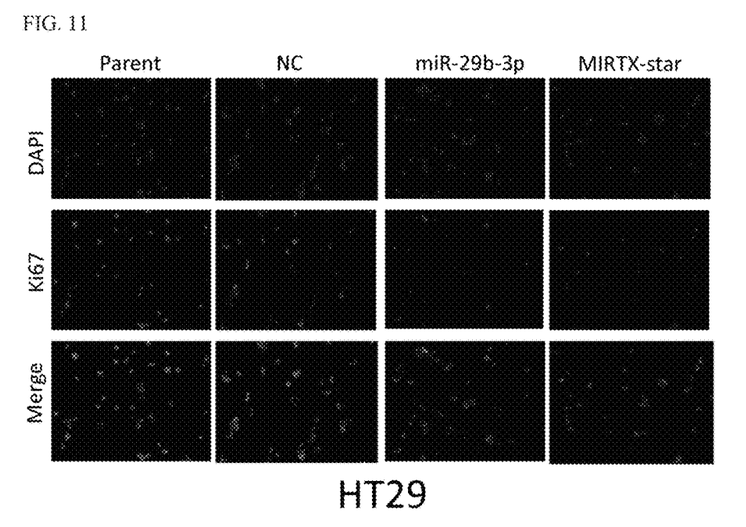
FIG. 11 shows results of Example 4, namely, the results of DAPI staining and Ki-67 immunostaining of human colorectal cancer cells (the strain HT29) cultured in the presence of the microRNA of the present invention.

FIG. 9 shows the results of cell numbers. FIG. 10 shows the results of microscopic observation of the state of the cell 72 hours after transfection. FIG. 11 shows the results of DAPI staining and Ki-67 immunostaining performed 48 hours after transfection. These results also showed that MIRTX-Star had an inhibitory effect on proliferation of the colorectal cancer cells and successfully inhibited proliferation of the colorectal cancer cells (the strain HT29).

Example 5: Evaluation of Antitumor Effect on Human Pancreatic Cancer Cells (Strain MIAPaCa-2)

An experiment was performed under the same conditions as in Example 1 except that a human pancreatic cancer cell (the strain MIAPaCa-2) was used.

Figure 12:
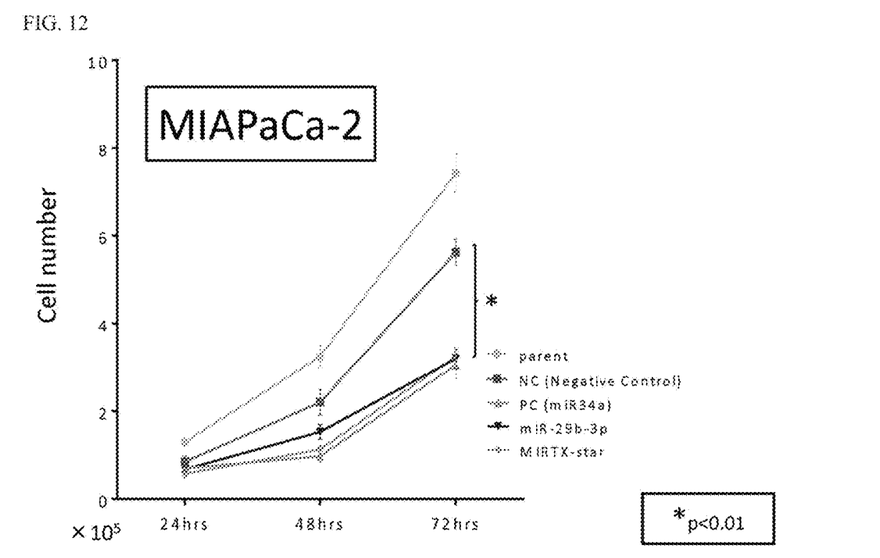
FIG. 12 shows results of Example 5, evaluating an inhibitory effect of the microRNA of the present invention on proliferation of human pancreatic cancer cells (the strain MIAPaCa-2).
Figure 13:
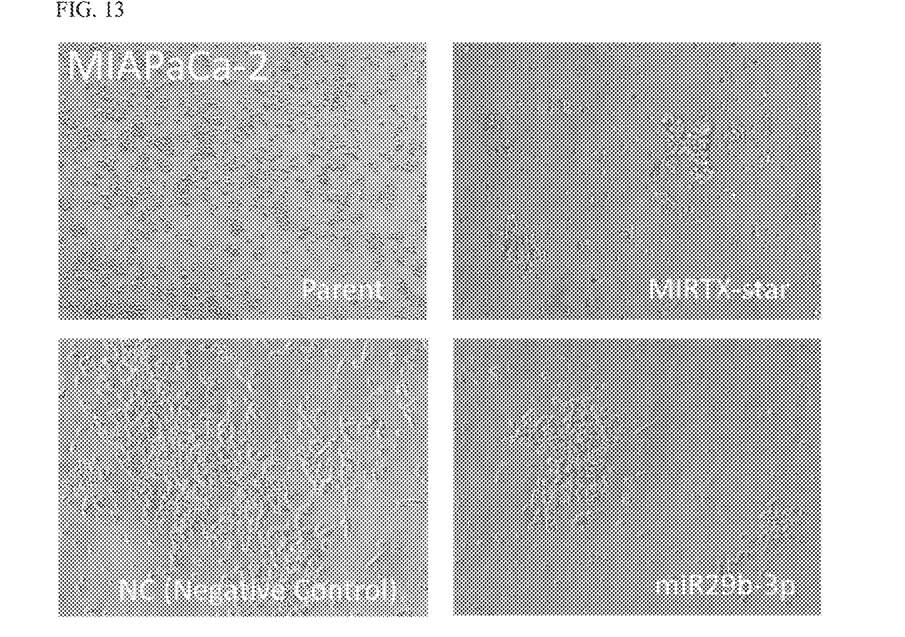
FIG. 13 shows results of Example 5, observing the phenotype of human pancreatic cancer cells (the strain MIAPaCa-2) after culturing the cells in the presence of the microRNA of the present invention.

FIG. 12 shows the results of cell numbers. FIG. 13 shows the results of microscopic observation of the phenotype of the cell 72 hours after transfection. These results also showed that MIRTX-Star had an excellent antitumor effect and effectively inhibited proliferation of the pancreatic cancer cells (the strain MIAPaCa-2).

Example 6: Evaluation of Antitumor Effect on Human Pancreatic Cancer Cells (Strain Panc-1)

An experiment was performed under the same conditions as in Example 1 except that human pancreatic cancer cells (the strain Panc-12) was used.

Figure 14:
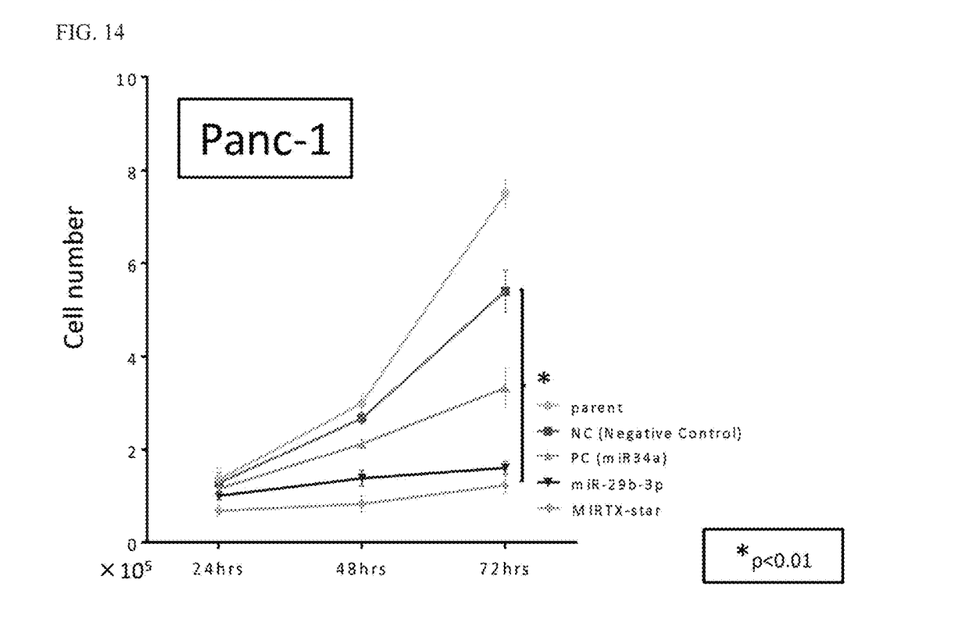
FIG. 14 shows results of Example 6, evaluating an inhibitory effect of the microRNA of the present invention on proliferation of human pancreatic cancer cells (the strain Panc-1).
Figure 15:
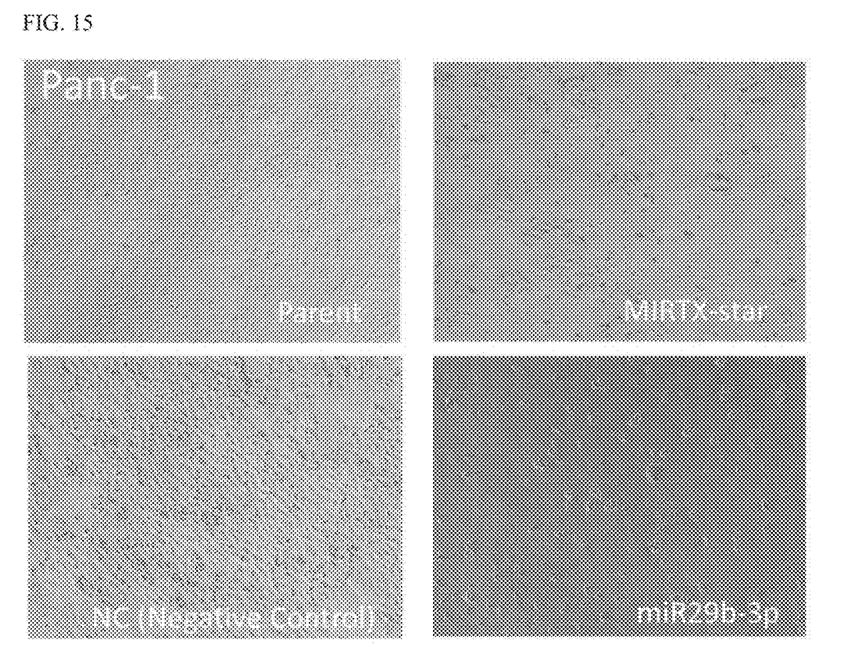
FIG. 15 shows results of Example 6, observing the state of human pancreatic cancer cells (the strain Panc-1) after culturing the cells in the presence of the microRNA of the present invention.

FIG. 14 shows the results of cell numbers. FIG. 15 shows the results of microscopic observation of the phenotype of the cells 72 hours after transfection. As shown in FIGS. 14 and 15, the antitumor effect of MIRTX-Star on the human pancreatic cancer cells (the strain Panc-1) was greater than that of miR-34a, and MIRTX-Star effectively suppressed proliferation of the pancreatic cancer cells (the strain Panc-1).

Example 7: Evaluation-1 of Therapeutic Effect on Colorectal Cancer Exhibited In Vivo by Complex Particles of MIRTX-Star and Carbonate Apatite Particles In a medium/Matrigel solution that contained Matrigel (BD Biosciences, San Jose, Calif.) and a medium at a volume ratio of 1:1, human colorectal cancer cells (the strain HT29) cell were mixed at a proportion of $2.5 \times 10^6$ cells per 100 μL. The resulting mixture was subcutaneously injected into a female nude mouse (NIHON CLEA, Tokyo, Japan), into the left side and the right side of the lower back (200 μL, each to the left and the right). On Day 0 when the HT29 cancer cells were administered, and Day 2, 4, 7, 9, 12, 14, and 16, a preparation including complex particles of MIRTX-Star obtained above and carbonate apatite particles (sCa-MIRTX) to be obtained below was injected into the caudal vein, in an amount such that a single dose contained 40 μg of MIRTX-Star. For comparison in this experiment, a case in which no complex particles of MIRTX-Star and carbonate apatite particles were introduced (Parent) and a case in which a control microRNA (SEQ ID NO: 2) were used instead of MIRTX-Star (sCa-control-miR) were also performed under the same conditions.

(Method of Preparing Preparation Including Complex Particles of MIRTX-Star and Carbonate Apatite Particles)

To 100 ml of distilled water, 0.37 g of $NaHCO_3$, 90 μl of $NaH_2PO_4.2H_2O$ (1 M), and 180 μl of $CaCl_2$ (1 M) were added in this order for dissolution, followed by pH adjustment with 1 N HCl to pH7.5. The resulting mixture was filtrated through a filter with a diameter of 0.2 μm. To 1 ml of the resulting buffer, 2 of MIRTX-Star and 4 μl of $CaCl_2$ (1 M) were mixed, followed by incubation in a water bath at 37° C. for 30 minutes. After centrifugation at 15000 rpm for 5 minutes, the resulting pellet was dispersed in physiological saline solution. As a result, a dispersion was obtained that contained complex particles in which MIRTX-Star was contained within carbonate apatite particles. The resulting dispersion was subjected to ultrasonic vibration treatment for 10 minutes. As a result, a preparation was obtained that included a complex of MIRTX-Star and carbonate apatite nanoparticles containing the MIRTX-Star. The ultrasonic vibration treatment was performed in a water bath having an ultrasonic vibration function, where a plastic container containing the dispersion solution obtained above was made floating in water at 20° C. in the water bath. The ultrasonic vibration treatment was continued for 10 minutes under conditions of a high-frequency power of 55 W and an oscillating frequency of 38 kHz. The resulting preparation was immediately subjected to the test described above. Measurement with a scanning probe microscope showed that the average particle size of the complex of MIRTX-Star and carbonate apatite nanoparticles containing the MIRTX-Star in the resulting preparation was 50 nm or less.

Figure 16:
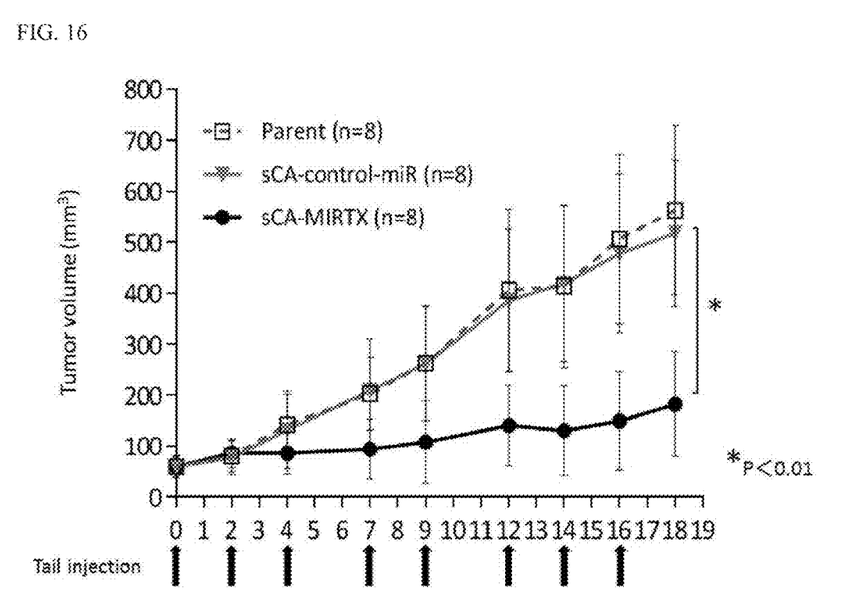
FIG. 16 shows results of Example 7 in colorectal cancer cells, evaluating the influence of complex particles of the microRNA of the present invention and carbonate apatite particles on the tumor size.
Figure 17:
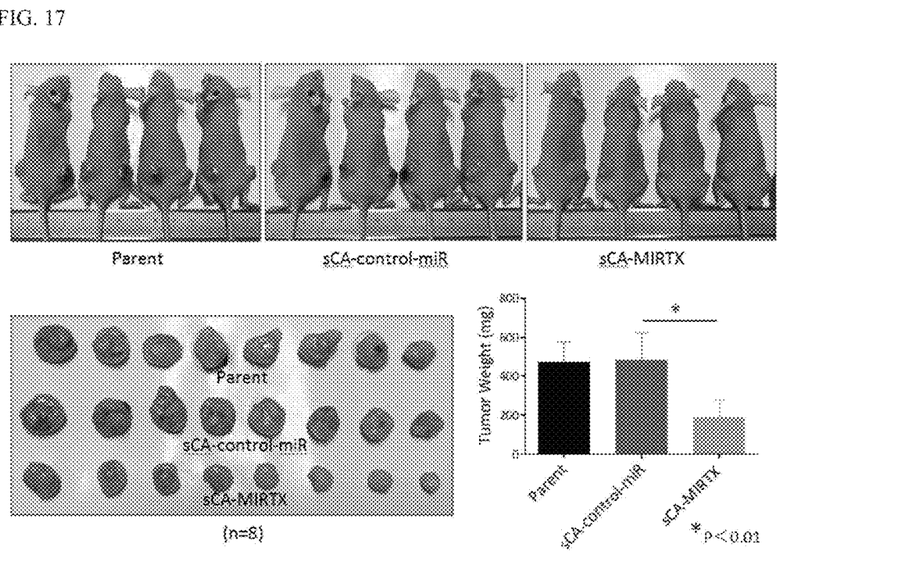
FIG. 17 shows results of Example 7 in a nude mouse that received subcutaneous injection of human colorectal cancer cells and also received a predetermined number of doses of complex particles of the microRNA of the present invention and carbonate apatite particles, namely, the Day-18 results of observation of the back of the mouse, observation of tumor taken from the mouse, and measurement of the tumor weight.

From the point of time when the HT29 cancer cells were administered, the size of tumor on the back of the mouse was measured with time (longer diameter×shorter diameter× shorter diameter×½). The results are shown in FIG. 16. FIG. 17 shows the results of observation of the back of the mouse on Day 18, observation of the tumor taken from the mouse on Day 18, and measurement of the weight of the tumor taken from the mouse on Day 18.

As shown in FIGS. 16 and 17, when the complex particles of MIRTX-Star and carbonate apatite particles were administered, the growth of the HT29 cancer cells was significantly inhibited, indicating a remarkable antitumor effect.

Example 8: Evaluation of In Vivo Safety of MIRTX-Star

In order to evaluate safety of MIRTX-Star the following experiments were performed. The preparation including complex particles of MIRTX-Star and carbonate apatite particles used in Example 7 was injected into the caudal vein of a female nude mouse (NIHON CLEA, Tokyo, Japan) in an amount such that a single dose contained 40 μg of MIRTX-Star, on Day 1, 2, 4, 7, 9, 12, 14, and 16. For comparison in this experiment, a case in which no complex particles of MIRTX-Star and carbonate apatite particles were introduced (Parent) and a case in which a control microRNA (SEQ ID NO: 2) was used instead of MIRTX-Star (sCa-control-miR) were also performed under the same conditions. The body weight of the nude mouse was measured with time. On Day 18, a blood chemistry analysis and HE (Hematoxylin and Eosin) staining of each organ were performed.

Figure 18:
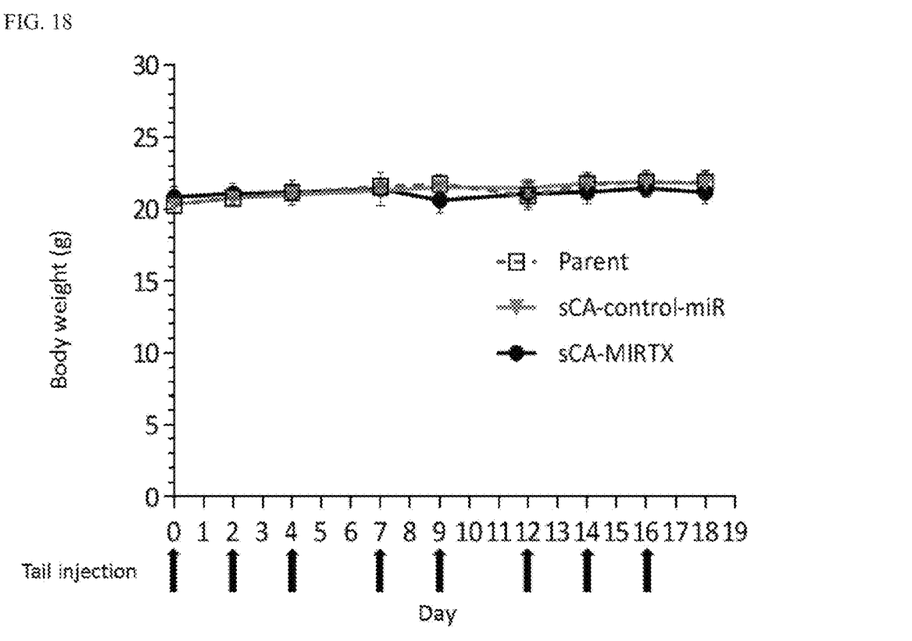
FIG. 18 shows results of Example 8, namely, the time-course results of body weight of a nude mouse that was administered with complex particles of the microRNA of the present invention and carbonate apatite particles.
Figure 19:
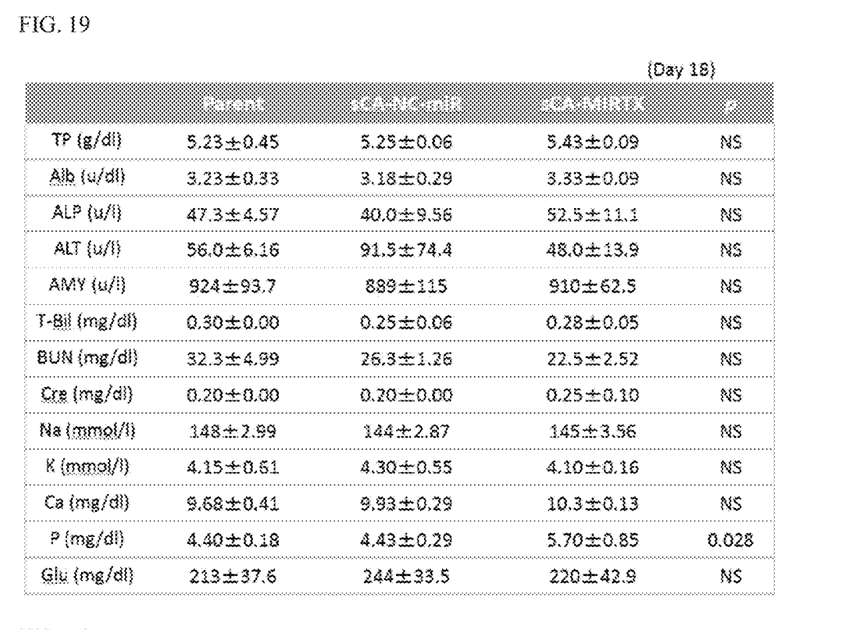
FIG. 19 shows results of Example 8, namely, the results of blood chemistry analysis in a nude mouse that was administered with complex particles of the microRNA of the present invention and carbonate apatite particles.
Figure 20:
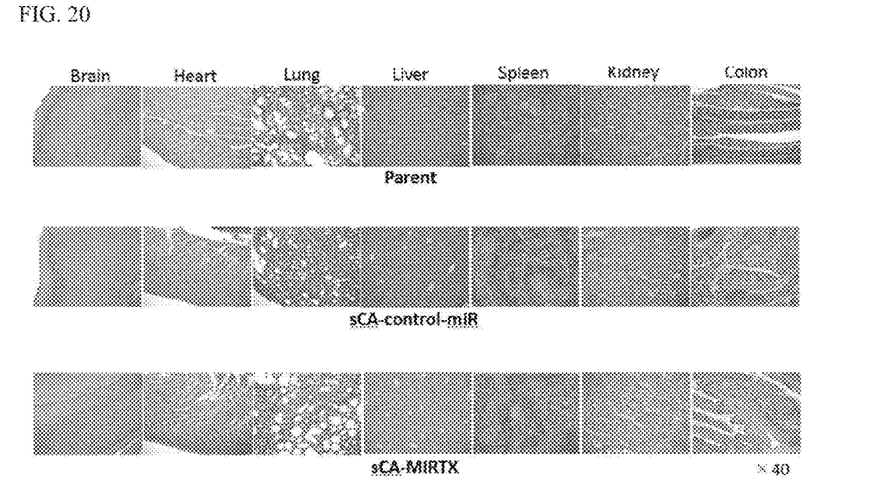
FIG. 20 shows results of Example 8, namely, the results of HE (Hematoxylin and Eosin) staining of various organs of a nude mouse that was administered with complex particles of the microRNA of the present invention and carbonate apatite particles.

The time-course results of body weight are shown in FIG. 18. The results of the blood chemistry analysis are shown in FIG. 19. The results of HE staining of each organ are shown in FIG. 20. In the group that received administration of the complex particles of MIRTX-Star and carbonate apatite particles, no mice died and almost no change were observed in the body weight compared to the other group. The results of the blood chemistry analysis showed no significant difference between the group that received administration of the complex particles of MIRTX-Star and carbonate apatite particles and the other group. The results of the HE staining of each organ showed no histological damage sustained by the group that received administration of the complex particles of MIRTX-Star and carbonate apatite particles. These results indicated that MIRTX-Star had excellent safety.

The invention claimed is:

1. A microRNA, comprising:
a polynucleotide having a base sequence represented by SEQ ID NO: 1 but comprising a substitution or deletion of at least one base selected from the group consisting of the 1st, 14th, 20th, and 24th base from the 5' end of the base sequence represented by SEQ ID NO: 1, the substitution being substitution by another base(s), and the polynucleotide (ii) having a comparable level of antitumor effect to the antitumor effect of the polynucleotide consisting of the base sequence represented by SEQ ID NO:1.

2. The microRNA according to claim 1, wherein the microRNA is a mature miRNA, a pri-miRNA, or a pre-miRNA.

3. A therapeutic agent for cancer, comprising the microRNA as claimed in claim 1 as an active ingredient.

4. The therapeutic agent for cancer according to claim 3, wherein the microRNA is in the form of a complex with carbonate apatite particles.

5. A method of treating a cancer, comprising:
a step of administering an effective amount of a microRNA comprising a polynucleotide having a base sequence represented by SEQ ID NO: 1 or the microRNA according to claim 1 to a cancer patient, wherein the cancer is a colorectal cancer or a pancreatic cancer.

6. A method of producing a therapeutic agent for cancer comprising obtaining a microRNA according to claim 1.

* * * * *

SEQUENCE LISTING

```
<160> NUMBER OF SEQ ID NOS: 5

<210> SEQ ID NO 1
<211> LENGTH: 24
<212> TYPE: RNA
<213> ORGANISM: Artificial Sequence
<220> FEATURE:
<223> OTHER INFORMATION: MIRTX-Star

<400> SEQUENCE: 1
ucuaaaccac cauaugaaac cagc                                                24

<210> SEQ ID NO 2
<211> LENGTH: 21
<212> TYPE: RNA
<213> ORGANISM: Artificial Sequence
<220> FEATURE:
<223> OTHER INFORMATION: Control microRNA

<400> SEQUENCE: 2
auccgcgcga uaguacguau u                                                   21

<210> SEQ ID NO 3
<211> LENGTH: 22
<212> TYPE: RNA
<213> ORGANISM: Homo sapiens

<400> SEQUENCE: 3
uggcaguguc uuagcugguu gu                                                  22

<210> SEQ ID NO 4
<211> LENGTH: 23
<212> TYPE: RNA
<213> ORGANISM: Homo sapiens

<400> SEQUENCE: 4
uagcaccauu ugaaaucagu guu                                                 23

<210> SEQ ID NO 5
<211> LENGTH: 24
<212> TYPE: RNA
<213> ORGANISM: Artificial Sequence
<220> FEATURE:
<223> OTHER INFORMATION: polynucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (14)..(14)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u
<220> FEATURE:
<221> NAME/KEY: misc_feature
<222> LOCATION: (24)..(24)
<223> OTHER INFORMATION: n is a, c, g, or u

<400> SEQUENCE: 5
ncuaaaccac caunugaaan cagn                                                24
```